United States Patent [19]

Percel

[11] Patent Number: 4,719,114

[45] Date of Patent: Jan. 12, 1988

[54] ENCAPSULATED YEAST

[75] Inventor: Phillip J. Percel, Olmsted Falls, Ohio

[73] Assignee: Durkee Industrial Foods, Corp., Iselin, N.J.

[21] Appl. No.: 688,839

[22] Filed: Jan. 4, 1985

[51] Int. Cl.$^4$ .................... C12N 1/16; C12N 1/04; C12N 1/18; A23L 1/28

[52] U.S. Cl. ................................... 426/62; 435/255; 435/256; 435/260

[58] Field of Search ............... 435/188, 255, 256, 260, 435/942; 426/61, 62

[56] References Cited

U.S. PATENT DOCUMENTS

| | | | |
|---|---|---|---|
| 2,523,483 | 9/1950 | Stern | 99/94 |
| 2,894,842 | 7/1959 | Mitchell, Jr. et al. | 99/96 |
| 3,407,072 | 10/1968 | Aizawa et al. | 435/260 |
| 3,843,800 | 10/1974 | Langejan | 426/18 |
| 4,217,420 | 8/1980 | Langejan | 435/256 |
| 4,226,940 | 10/1980 | Starrs | 435/260 |
| 4,245,039 | 1/1981 | Heimburger et al. | 435/260 |
| 4,341,871 | 7/1982 | Langejan | 435/256 |

OTHER PUBLICATIONS

"Active Dry Yeast: Protection Against Oxidative Deterioration During Storage", Chen et al, Food Technology, Dec., 1966, vol. 20, No. 12, pp. 79–83.

Primary Examiner—Esther M. Kepplinger
Attorney, Agent, or Firm—Richard H. Thomas

[57] ABSTRACT

A process for preserving active dry yeast comprising applying polyethylene glycol having a molecular weight in the range of about 3350 to about 4600 to the surface of said yeast in a preserving amount.

8 Claims, No Drawings

ENCAPSULATED YEAST

The present invention relates to a method for the preparation of stable active dry yeast, and to yeast products so prepared. The present invention is particularly concerned with the encapsulation of what is referred to as "instant" active dry yeast.

The present invention will be particularly described with respect to active dried yeast suitable for breadmaking, although it will be apparent to those skilled in the art that the present invention has other applications, such as baking dry mixes (e.g., Danish pastries, bread, donuts, sweet dough, pizza, rolls and buns) and dry mixes for wine making.

BACKGROUND OF THE INVENTION

Active dried yeast is prepared in a dry, granular form by drying extruded, compressed yeast under carefully controlled conditions to a moisture content of about 7.5 to 8.5%. An advantage with active, dry yeast is that it does not require refrigeration to maintain its activity, and the shelf life can vary from one to twelve months, depending upon ambient storage conditions, the stability being inversely related to storage temperature and moisture content.

There has recently been developed an active dried bakers' yeast which is said to have considerably higher fermentative activity than traditional active dry yeasts. It is also said to have an oblong porous structure which permits its use in doughs without prior rehydration. The yeast is marketed by Gist-Brocades U.S.A., Inc. under the trademark Fermipan, as an instant active dried yeast and is described in U.S. Pat. Nos. 4,217,420; 3,843,800; and 4,341,871. The yeast is normally packaged under vacuum, and once the package is opened, the yeast has to be used within three days. When premixed with flour, special precautions have to be taken to insure minimum contact of the yeast with moisture. Vacuum packing or packing in a nitrogen atmosphere is also recommended for the dry mixes containing the yeast.

Prior U.S. Pat. No. 2,894,842 to Mitchell et al, refers to the improved thermostability and storage stability achieved by drying to lower than 7.5 to 8.5% moisture content, for instance about 3-4%. U.S. Pat. No. 2,894,842 is directed to the problem of rehydrating yeast having such low moisture content, and teaches adding a lipophilic substance such as an aliphatic partial ester of sorbitan to the yeast prior to dehydration.

In a paper by Chen et al, entitled "Active Dry Yeast: Protection Against Oxidative Deterioration During Storage", Food Technology, December, 1966, Volumn 20, No. 12, pages 79-83, it is pointed out that even at the lower levels of 3-4% moisture content, the deteriorative effect of oxygen is not eliminated.

Prior U.S. Pat. No. 2,523,483 describes coating yeast with shortening to preserve the yeast. Examples of shortening described in the patent are lard and animal fat, preferably hydrogenated fat. The dried yeast is granulated to a size about the same as sugar, and to a moisture content such that it feels dry. The dried yeast is then mixed with the fat, either by hand or in a cake mixer, or the equivalent. The shortening can be in a melted or solid condition, and mixing is carried out to ensure that each yeast granual is completely covered with fat.

The problem with the use of a solid fat or shortening is that the same is not cold-water soluble, and, as stated in U.S. Pat. No. 2,523,483, warm water should be added to the coated yeast at a sufficiently high temperature to quickly melt the fat from the yeast and free the yeast particles to permit them to hydrate and commence fermentation.

In this regard, it is critical to avoid exposing the yeast, either at the time of application of a coating or at the time of removal of the coating, to temperatures so high so as to kill at least a part of the yeast. In U.S. Pat. No. 2,523,483, the yeast was not exposed to the high temperatures of molten lard or animal fat during coating, but rather coating was carried out by the cruder or less sophisticated method of simple mixing with the plastic material.

In U.S. Pat. No. 2,523,483, it is also pointed out that the yeast, during removal of the coating, is protected from the hot water by the coating, the implication being that some yeast could be killed even from the temperature of water which is too hot.

It has also been proposed to coat water-sensitive materials with aqueous-based coatings, under carefully controlled conditions, but the problem here is that even with the carefully controlled conditions, the yeast in the coating process would pick up too much moisture, adversely affecting its shelf life or stability.

DISCLOSURE OF THE INVENTION

The present invention resides in the discovery that the above disadvantages, can be overcome by encapsulating or coating active dried yeast with a water-soluble, polyethylene glycol, having a molecular weight in the range of about 3,350 to about 8,000 and a melting point in the range of about to about 54° C. to about 63° C. The coating weight is that effective to achieve shelf life stability.

A preferred polyethylene glycol is one having a molecular weight in the range of about 3,350 to about 4,600.

Coating is preferably carried out in a fluid bed apparatus by spray applying molten polyethylene glycol onto the surface of yeast particles which are in a fluidized state.

BEST MODE FOR CARRYING OUT THE INVENTION

The present invention is based on the discovery of a class of compounds capable of application to active dry yeast particles under conditions in which a film or coating can be formed on the particles, without exposing the dry yeast to water, the compounds, however, being infinitely cold-water soluble, permitting substantially instantaneous rehydration of the yeast at time of use. By the language "under conditions to form a film or coating", it is meant that the compounds can be applied to the surface of the active dry yeast in yeast-preserving amounts. It is also an aspect of the present invention that the compounds herein permit application to the surface of the yeast particles under conditions which avoid injury to the yeast.

The Active Dry Yeast

Two types of baking yeast are produced commercially: compressed yeast and active, dry yeast. The former contains about 68-72% moisture and requires refrigerated storage. Even then, it has a limited shelf life of only about 3-5 weeks. Active, dry yeast is a dehydrated form of baking yeast having a moisture content of less than about 10%.

There are a number of methods for preparing active, dry yeast, for instance, by extrusion into pellet form, followed by drum drying, or by spray drying a liquid yeast composition in air, to producd powdered yeast. By way of example, a liquid yeast containing less than 27% dry material may be spray dried to a moisture content of, for example, 40–50% dry matter, and may then be further dried by, for example, fluidized bed drying.

Active, dry yeast, particularly yeast strains suitable for leavening, are extremely delicate and sensitive to changes in environment. For instance, rehydration of the dry yeast, using water temperature greater or less than about 110 degrees F., can substantially reduce the yeast activity. Thus, the shelf life of active, dry yeast can vary anywhere from about 1 month to 12 months, depending upon ambient storage conditons, the stability being inversely related to storage temperature and moisture content. Even the presence of atmospheric oxygen can have a deleterious affect on the stability of active dried yeast.

The presence of a substantial proportion of dead or weakened cells results in reduction of the leavening activity of the yeast and also has an undesirable affect on the quality of goods baked with it, as evidenced by poor volume and poor texture of the finished baked goods.

The yeast to which the present invention is primarily directed is an "instant" active dried yeast marketed by Gist-Brocades U.S.A., Inc. under the trademark "Fermipan". However, it will be apparent to those skilled in the art that the present invention is applicable broadly to the protection of all active dry yeasts. The same advantages of the present invention will pertain.

The "Fermipan" yeast is marketed as a dry yeast with considerably higher fermentative activity than traditional active dry yeasts. It is a strain of the species *Saccharomyces cerevisiae*, which is produced by a special fermentation process and a patented drying process. The yeast consists of small oblong particles with a porous structure. This permits its use in dough without prior rehydration. It is packaged under vacuum, resulting in a solid hard package. Once the package is opened, it becomes a free-flowing granular powder. After opening the package, it normally should be used within three days.

Prior U.S. Pat. No. 4,217,420 describes the yeast as an active dried bakers' yeast with a particle size of 0.1 to 1.0 mm, with a dry matter content of at least 85% by weight, a protein content of 45–60% based on dry matter and an activity value of 420 to 600 when determined by a test method described in the patent specification. The yeast is prepared by the steps of dividing a fresh compressed yeast having a protein content of 45–60%, on a dry weight basis, into a mass of particles having a particle size of 0.2 to 2.0 mm and drying the mass of particles by passing therethrough a drying gas at a temperature of not more than 160° C. in not more than 120 minutes to a dry matter content of at least 85% by weight with a drying gas flow so that the particles are held within a temperature range of from 20°–50° C. The compressed yeast prior to drying has added to it at least one member selected from the group consisting of: 0.51–5%, based on dry matter of the yeast, of a swelling agent in turn selected from the group consisting of methyl cellulose and carboxymethyl cellulose; and 0.5–5%, based on dry matter of the yeast; of a wetting agent selected in turn from the group consisting of an ester of a saturated and unsaturated fatty acid, a fatty acid ester of glycerol, a fatty acid ester of propylene glycol and a mixture of two or more thereof. The yeast has the advantages that it can be added as such to flour prior to dough making without preliminary soaking, and it is capable of better gas production than active dried yeasts hitherto available. For instance, one pound of Fermipan is said to be capable of replacing three pounds of compressed yeast, or 1.6 pounds of traditional active dry yeast. Where Fermipan is used is prepared mixes, i.e., the Fermipan is premixed with the flour, salt, shortening, sugar, milk powder, etc., special attention has to be given to the moisture content of the flour, the type of sugar used, water absorption of the mix, packaging, and shelf-life of the mix.

The moisture of the flour will cause a rapid deterioration in the Fermipan activity. It is essential, therefore, that a specially dried flour of approximately 6% moisture content be used. The extra drying of the flour will cause it to be more expensive than ordinary flour.

Dextrose or corn sugar has a moisture content of approximately 9%, while powdered sugar, cane or beet sugar, etc., contain no appreciable moisture. In order to help decrease the moisture content of the mix and thereby increase its shelf-life, one of the latter sugar types rather than dextrose or corn sugar is recommended.

When the mix is exposed to humidity, it will result in a decrease in its shelf-life. Special care is recommended with regard to packaging. The use of a vacuum pack or of gas flushing with nitrogen is said to greatly improve shelf-life. Basically, the moisture content of the mix should be maintained below 8%.

When the above requirements have been met, it is advertised that a prepared mix can be marketed with a shelf-life of approximately 6 months. Shelf-life of the prepared mix can be improved by storage temperatures of approximately 40° F.

The Coating Compositions

The coating compositions of the present invention are medium weight polyethylene glycols having a molecular weight in the range of about 3,350 to about 8,000. These polymers are white, waxy solids which are soluble in water, as well as in many of the more polar, non-aqueous solvents, or in mixtues of the polar solvents with non-polar, organic solvents. They have freezing points in the range of about 54 degrees to about 63 degrees C.

Several particularly suitable polymers are available. One is sold as "Carbowax 4600", marketed under this trademark by Union Carbide Corporation. Others are "Carbowax 3350" and "Carbowax 8000", also marketed by Union Carbide Corporation.

Of these, the higher molecular weight polymers offer somewhat more abrasion resistence. Which coating is preferred depends upon end use. Some abrasion, in certain uses, may be desirable to optimize rehydration of the yeast.

The following is pertinent data concerning suitable polyethylene glycols:

| Carbowax Poly- ethylene Glycols | Average Molecular Weight | Melting or Freezing Range, °C. | Viscosity at 210° F. Centistokes | Physical Form |
|---|---|---|---|---|
| 3350 | 3350 | 54 to 58 | 75 to 110 | molten, flake or powder |
| 4600 | 4600 | 57 to 61 | 160 to 230 | molten or flake |
| 8000 | 8000 | 60 to 63 | 700 to 900 | molten, flake or powder |

Selected Properties

In the practice of the present invention, the polyethylene glycol coatings are applied in a preserving amount (the amount necessary to significantly increase yeast shelf life), preferably at a coat weight so that they comprise about 15% to about 40% percent of the total yeast coated product. At higher coat weights, insufficient additional protection is obtained to justify the added cost. At lower coat weights, inadequate protection is provided.

Within the preferred coat weight range, a shelf life of several weeks can be obtained with the Fermipan yeast, compared to a conventional shelf life of a few days.

Procedure of The Present Invention

In the practice of the present invention, a preferred method is to coat the yeast by fluidizing it and spraying molten polyethylene glycol into the fluidized bed. An example of a fluidized bed spray applicator which may be used is one shown in U.S. Pat. No. 3,913,847. In general, the apparatus is provided with a cylindrically shaped chamber, preferably with an expansion zone at the top of the chamber to limit the elevation of the bed. The bottom of the bed is maintained by an air distribution plate extending horizontally across the chamber near the bottom of the chamber.

Inlet air is introduced into the bottom of the chamber as a fluidizing medium. A spray nozzle for spraying the polyethylene glycol is positioned above the level of the bed or in the bed. In operation, the polyethylene glycol is first reduced to a molten state and then is sprayed onto the bed through the spray nozzle. A suitable temperature range for most applications for the polyethylene glycol is about 85°–100° C. The polyethylene glycol should be at a sufficiently high temperature to flow over the surface of the particles of yeast, but at the same time, at a sufficiently low temperature to avoid adversely affecting the yeast. It is an unexpected aspect of the present invention that the subject polyethylene glycols meet both criteria.

The velocity of the fluidizing medium in the chamber is that necessary to establish the fluid bed and will be well known to those skilled in the art. The temperature of the fluidizing medium also should be that necessary to avoid injury to the live yeast culture.

A particular fluidized bed spray applicator that can be employed is one marketed by Glatt Air Techniques, Inc., Ramsey, N.J., Model GPCG-30. A similar apparatus is marketed by Aeromatic, Inc., of Bernardsville, N.J.

The present invention is illustrated in the following example:

EXAMPLE 1

"Fermipan" active dry yeast was coated in a Glatt Agglomerator, Model GPCG-30 fluidized bed. The following coatings and coating levels were used

| Coating | Coating levels % by weight based on total particle weight | | |
|---|---|---|---|
| Durkee KLX* | 15 | 30 | 40 |
| Sodium stearoyl lactylate (SSL) | 15 | 30 | 40 |
| Durkee Dur-em 207E** | 15 | 30 | 40 |
| Durkee SSL/207E in a 20/80 ratio | 15 | 30 | 40 |
| Union Carbide Carbowax 4600 | 15 | 30 | 40 |

*Trademark SCM Corporation, a partially hydrogenated soybean/cottonseed oil stearine having a Capillary Melting Point of 124–130° F.
**Trademark SCM Corporation, a finely divided mono-diglyceride having an alpha monoglyceride content of at least 50% and a Capillary Melting Point of about 140–146° F.

Carbowax 4600 was applied as a hot melt system, yet is readily soluble in water. Sodium stearoyl lactylate and Dur-em 207E (mono-diglyceride) were also applied as a hot melt but are water dispersible and not water soluble. Durkee KLX is not water soluble. All coatings gave a certain degree of moisture impermeability. Only the Carbowax 4600 was readily released in cold water.

The Carbowax-coated yeast particles, at 30% coating level, gave a shelf life, in a dry mix, of at least four weeks using an accelerated test procedure, far in excess of that achieved with uncoated yeast particles. Similar shelf life was achieved at the other coating levels. The particles were also resistant to abrasion and coating loss during end use mixing, substantially more so than the fat-coated particles, also improving shelf life.

The following is U.S. Standard Sieve particle-size data on the yeast particles before coating and the Carbowax-coated yeast particles:

| Pan No. | Sieve Opening (microns) | Uncoated Yeast | | Coated Yeast | |
|---|---|---|---|---|---|
| | | wght. | percent | wght. | percent |
| 10 | 2000 | .00 | 0.00 | 0.00 | 0.00 |
| 20 | 850 | .01 | 0.02 | 2.40 | 4.91 |
| 40 | 425 | 11.94 | 24.29 | 39.89 | 81.56 |
| 60 | 250 | 34.92 | 71.04 | 6.28 | 12.84 |
| 80 | 180 | 1.32 | 2.68 | 0.22 | 0.45 |
| 100 | 150 | 0.35 | 0.71 | 0.05 | 0.10 |
| Pan | | 0.62 | 1.26 | 0.07 | 0.14 |
| | | 49.16 | 100.00 | 48.91 | 100.00 |

During the coating, the above data shows that there was only a slight mean particle size increase from a number 60 sieve to a number 40 sieve. The data is indicative of little or no agglomeration during coating.

I claim:

1. A process for preserving active dry yeast comprising applying polyethylene glycol having a molecular weight in the range of about 3350 to about 4600 to the surface of said yeast in a preserving amount.

2. The process of claim 1 wherein said coating is carried out in a fluid bed applicator, said preserving amount being about 15–40% of the total particle weight.

3. The process of claim 2 wherein said coated yeast has an average particle size in the range of about 20 to about 80 mesh, U.S. Standard Sieve.

4. The process of claims 1, or 2 or 3 wherein said yeast is instant active dry yeast.

5. An active dry yeast coated with water soluble polyethylene glycol having a molecular weight in the range of about 3350 to about 4600, the amount of polyethylene glycol being a preserving amount.

6. The dry yeast of claim 5 wherein said coating is carried out in a fluid bed applicator, said preserving amount being about 15–40% of the total particle weight.

7. The dry yeast of claim 6 wherein said coated yeast has an average particle size in the range of about 20 to about 80 mesh, U.S. Standard Sieve.

8. The dry yeast of claims 5, or 6, or 7 wherein said yeast is instant active dry yeast.

* * * * *